(12) United States Patent
Choi et al.

(10) Patent No.: US 7,566,755 B2
(45) Date of Patent: Jul. 28, 2009

(54) COMPOUND AND COMPOSITION PRODUCED BY USING SUCH COMPOUND

(75) Inventors: Wonmun Choi, Kanagawa (JP); Daisuke Kanenari, Kanagawa (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 402 days.

(21) Appl. No.: 10/546,769

(22) PCT Filed: Feb. 20, 2004

(86) PCT No.: PCT/JP2004/001964

§ 371 (c)(1),
(2), (4) Date: Aug. 24, 2005

(87) PCT Pub. No.: WO2004/074250

PCT Pub. Date: Sep. 2, 2004

(65) Prior Publication Data

US 2006/0155078 A1   Jul. 13, 2006

(30) Foreign Application Priority Data

Feb. 24, 2003 (JP) ............................. 2003-045405
Nov. 14, 2003 (JP) ............................. 2003-384762

(51) Int. Cl.
*C08F 8/34* (2006.01)
(52) U.S. Cl. .............. 525/327.5; 525/328.9; 525/332.7; 525/332.8; 525/332.9; 525/333.1; 525/348
(58) Field of Classification Search .............. 525/327.5, 525/328.9, 332.7, 332.8, 332.9, 333.1, 348
See application file for complete search history.

(56) References Cited

U.S. PATENT DOCUMENTS

| 4,775,463 | A | 10/1988 | Halinen et al. | |
|---|---|---|---|---|
| 5,102,568 | A | * | 4/1992 | King et al. ............ 508/274 |
| 5,145,970 | A | | 9/1992 | Pastor |
| 5,804,668 | A | | 9/1998 | Schubart et al. |
| 2004/0260038 | A1 | | 12/2004 | Choi |

FOREIGN PATENT DOCUMENTS

| GB | 998973 A | 7/1965 |
|---|---|---|
| JP | 01-094346 A | 4/1989 |
| JP | 10-053667 A | 2/1998 |
| JP | 2001-158824 A | 6/2001 |
| JP | 2001-316527 A | 11/2001 |
| WO | WO-03/040133 A1 | 5/2003 |

OTHER PUBLICATIONS

Marrian, D. H., "Reactions of Substituted Maleimides with Thiols", Journal of the Chemical Society,(1949). 1515-16.*
English Translation of International Perlminary Report Dated Feb. 13, 2006.
PCT International Search Report for PCT/JP2004/001964 mailed on Apr. 27, 2004.
Chemical Abstracts, Jan. 25, 1950, vol. 44, No. 2, An:550g-i.

* cited by examiner

*Primary Examiner*—Bernard Lipman
(74) *Attorney, Agent, or Firm*—Connolly Bove Lodge & Hutz LLP

(57) ABSTRACT

An object of the present invention can be to provide a crosslinking agent which exhibits excellent storage stability and heat resistance and which is used for a composition containing a rubber and/or a resin. Such an object is realized by the compound represented by the following formula (1).

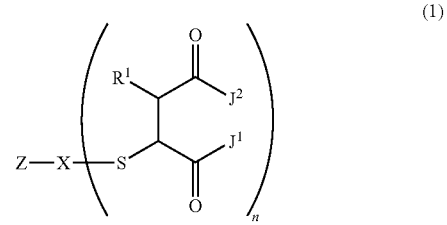

In the formula, Z represents an active hydrogen-containing group; X represents a non-cyclic aliphatic group, a cyclic aliphatic group, an aromatic group, or an alkyl aromatic group, which may be optionally substituted and which may contain at least one member selected from $SO_2$, O, N, and S; $J^1$ and $J^2$ which are respectively included at a number of n independently represent a monovalent group, or $J^1$ and $J^2$ together represent a divalent group; $R^1$ which is included at a number of n independently represents hydrogen atom or a non-cyclic aliphatic group; and n represents an integer of 1 to 4.

6 Claims, No Drawings

COMPOUND AND COMPOSITION PRODUCED BY USING SUCH COMPOUND

TECHNICAL FIELD

This invention relates to a novel compound which can be used as a crosslinking agent or a vulcanization agent for a composition containing a rubber and/or a resin, as well as a composition produced by using the novel compound.

BACKGROUND ART

A thiol compound having two or more thiol groups in one molecule is useful as a crosslinking agent for a composition containing a rubber and/or a resin such as a halogenated rubber, a halogenated resin, or an epoxy resin.

However, thiol group is a group having an extremely high reactivity, and it reacts with double bond, epoxy group, or other functional group in the rubber or the resin at room temperature in the presence of a catalyst such as a metal oxide or an amine compound. A thiol compound also often undergoes molecular weight increase, for example, by self-oxidation. Accordingly, use of such thiol compound for the crosslinking agent has been associated with the problems of inferior storage stability as well as the risk of reduced work productivity.

In the meanwhile, zinc oxide has been used as a crosslinking agent in the composition containing a rubber and/or a resin.

Use of a zinc oxide, however, has been associated with the problems of rubber scorching as well as inferior heat resistance of the resulting composition.

SUMMARY OF THE INVENTION

In view of the situation as described above, an object of the present invention is to provide a crosslinking agent which exhibits excellent storage stability and heat resistance and which can be used for a composition containing a rubber and/or a resin, as well as a composition produced by using such crosslinking agent.

The inventors of the present invention have found that a composition containing a rubber and/or a resin can be imparted with both excellent storage stability and excellent heat resistance if a compound having a thiol group protected by a maleimide compound and an active hydrogen-containing group is used for the crosslinking agent. The present invention has been completed on the bases of such findings.

Accordingly, the present invention provides the following (i) to (xii):

(i) A compound represented by the following formula (1) (hereinafter referred to as "the compound of the present invention").

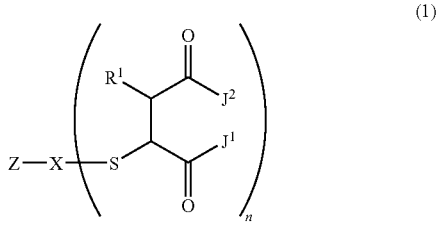

(1)

In the formula, Z represents an active hydrogen-containing group; X represents a non-cyclic aliphatic group containing 1 to 24 atoms (the number not including hydrogen), a cyclic aliphatic group containing 5 to 18 atoms (the number not including hydrogen), an aromatic or a heterocyclic group containing 6 to 18 atoms (the number not including hydrogen), or an alkyl aromatic group containing 7 to 24 atoms (the number not including hydrogen), which may be optionally substituted and which may contain at least one member selected from $SO_2$, O, N, and S; $J^1$ and $J^2$ which are respectively included at a number of n independently represent a monovalent group, or $J^1$ and $J^2$ together represent a divalent group; $R^1$ which is included at a number of n independently represents hydrogen atom or a non-cyclic aliphatic group containing 1 to 24 carbon atoms; and n represents an integer of 1 to 4.

(ii) A compound represented by the following formula (1').

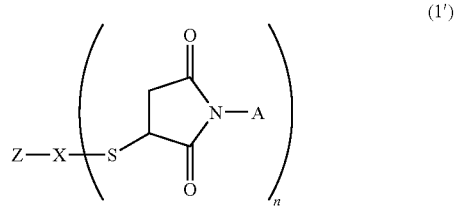

(1')

In the formula, Z represents an active hydrogen-containing group; X represents a non-cyclic aliphatic group containing 1 to 24 atoms (the number not including hydrogen), a cyclic aliphatic group containing 5 to 18 atoms (the number not including hydrogen), an aromatic group containing 6 to 18 atoms (the number not including hydrogen), or an alkyl aromatic group containing 7 to 24 atoms (the number not including hydrogen), which may be optionally substituted and which may contain at least one member selected from $SO_2$, O, N, and S; A which is included at a number of n independently represents an optionally substituted organic group containing 1 to 24 carbon atoms which does not contain active hydrogen group; and n represents an integer of 1 to 4.

(iii) The compound according to the above (i) or (ii) in which the active hydrogen-containing group represented by Z is thiol group, carboxy group, hydroxy group, imino group, or amino group.

(iv) A composition comprising:
the compound of any one of the above (i) to (iii), and
a rubber and/or a resin which has a functional group capable of reacting with thiol group and a functional group capable or reacting with the active hydrogen-containing group represented by Z (this composition is hereinafter referred to as "the composition of the present invention").

(v) The composition according to the above (iv) in which the rubber and/or the resin has at least one member selected from the group consisting of epoxy group, isocyanate group, oxetane group, halogen group, episulfide group, silyl group, acid anhydride group, unsaturated group, and maleimide group.

(vi) The composition according to the above (iv) or (v) further comprising magnesium oxide.

(vii) The composition according to any one of the above (iv) to (vi) comprising at least one member selected from diene rubber, halogenated rubber, maleic anhydride grafted rubber, and epoxized rubber as the rubber.

(viii) A composition comprising:

100 parts by weight of a rubber including rubber (A) containing a halogen group and/or an acid anhydride group, and containing 30 wt % or less of unsaturated bond, 0.1 to 20 parts by weight of the compound of any one of the above (i) to (iii), and at least one crosslinking agent selected from the group consisting of sulfur, organic peroxide, quinone dioxime, metal oxide, and alkylphenol-formaldenyde resin.

(ix) The composition according to the above (viii) comprising at least one member selected from the group consisting of halogenated butyl rubber, maleic anhydride grafted butyl rubber, maleic anhydride grafted ethylene-propylene copolymer rubber, maleic anhydride grafted ethylene-propylene-diene copolymer rubber, halogenated isobutylene-paramethylstyrene copolymer, chlorosulfonated polyethylene, epichlorohydrin rubber, fluoro rubber, and an acryl rubber having a halogen monomer copolymerized therein as the rubber (A).

(x) The composition according to the above (viii) or (ix) further comprising a sulfenamide or thiuram vulcanization accelerator.

(xi) A rubber laminate obtainable by disposing the composition according to any one of the above (viii) to (x) on a sulfur-vulcanizable rubber composition, and adhering these compositions by vulcanization (this rubber laminate is hereinafter referred to as "the rubber laminate of the present invention").

(xii) The compound according to any one of the above (iv) to (x) comprising an epoxy resin as the resin.

The compound of the present invention is extremely useful since the composition prepared by using such compound for the crosslinking agent of the rubber and/or the resin enjoys excellent storage stability as well as excellent heat resistance.

BEST MODE FOR CARRYING OUT THE INVENTION

First, the compound of the present invention is described.

The compound of the present invention is the compound represented by the formula (1) as described above. In the formula, Z represents an active hydrogen-containing group, which is not particularly limited as long as it is an active hydrogen-containing group. In view of the storage stability of the composition of the present invention, the active hydrogen-containing group is preferably the one containing one active hydrogen atom. Exemplary active hydrogen-containing group containing one active hydrogen atom include thiol group, carboxy group, hydroxy group, and imino group. An exemplary imino group is the one represented by —NHR$^2$ wherein R$^2$ represents an organic group containing 1 to 20 atoms (the number not including hydrogen) such as —NHC$_6$H$_5$.

When the composition of the present invention contains a rubber and/or a resin having a functional group (for example, isocyanate group) which reacts with an active hydrogen-containing group containing two active hydrogen atoms to leave no active hydrogen, an active hydrogen-containing group containing two active hydrogen atoms will not be associated with the problems of the insufficient storage stability problem, and use of such active hydrogen-containing group for Z is also preferable. An example of such active hydrogen-containing group containing two active hydrogen atoms is amino group.

The active hydrogen-containing group represented by Z may be selected by considering the vulcanization temperature at which the composition of the present invention is vulcanized. For example, when Z is a group having high electron withdrawing group as in the case of carboxy group, the vulcanization may be conducted at a relatively low temperature in view of the high likeliness of undergoing thermal dissociation (leaving of maleimide compound) as will be described below.

X may represent a non-cyclic aliphatic group containing 1 to 24 atoms (the number not including hydrogen), a cyclic aliphatic group containing 5 to 18 atoms (the number not including hydrogen), an aromatic group containing 6 to 18 atoms (the number not including hydrogen), or an alkyl aromatic group containing 7 to 24 atoms (the number not including hydrogen), which may be optionally substituted and which may contain at least one member selected from SO$_2$, O, N, and S. As evident from the formula (1), the valence of X is (1+n). The substituent is not particularly limited.

Examples of the X include ethylene group, hexamethylene group (—(CH$_2$)$_6$—), o-phenylene group, m-phenylene group, p-phenylene group, xylyl group, a divalent group having imidazol ring, a divalent group having naphthalene ring, a divalent group represented by the following formula (a), and the trivalent group represented by the following formula (b). Among these, the preferred are o-phenylene group, p-phenylene group, a divalent group represented by the following formula (a), and the trivalent group represented by the following formula (b), and the divalent group represented by the following formula (c).

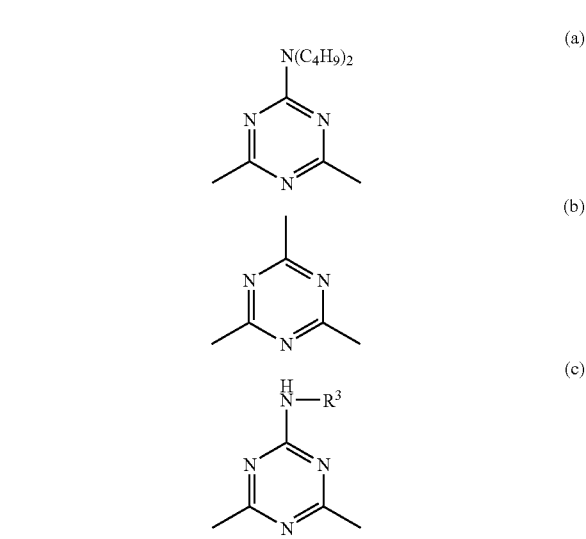

(In the formula, R$^3$ represents an organic group containing 1 to 24 carbon atoms.)

As in the case of Z, X may be selected by considering the vulcanization temperature at which the composition of the present invention is vulcanized.

J$^1$ and J$^2$ which are respectively included at a number of n independently represent a monovalent group, or J$^1$ and J$^2$ may together represent a divalent group, and n represents an integer of 1 to 4.

With regard to J$^1$ and J$^2$, J$^1$ and J$^2$ may respectively represent —OR$^4$ (wherein R$^4$ may independently represent an organic group containing 1 to 24 carbon atoms); J$^1$ and J$^2$ may together represent —NH—NH—; or J$^1$ and J$^2$ may together represent —NA- (A will be described below). Among these, J$^1$ and J$^2$ may preferably together represent —NA-. In other words, one preferable embodiment of the compound of the present invention is the compound represented by the formula (1').

In the above formula (1'), Z, X, and n may be as defined for formula (1).

A which is included at a number of n may independently represent an optionally substituted organic group containing 1 to 24 carbon atoms which does not contain active hydrogen group; and n may represent an integer of 1 to 4.

The organic group represented by A is not particularly limited, and exemplary organic groups include an alkyl group, a cycloalkyl group, an aryl group, and a group wherein one or more hydrogen atom thereof has been substituted with a substituent. Among these, the preferred are an aromatic group (such as phenyl group) and a cycloalkyl group.

The method used for producing the compound of the present invention is not particularly limited and any known method can be used. For example, a compound having thiol group and the active hydrogen-containing group represented by the Z as described above may be used with a maleimide compound represented by the following formula (2) to allow addition of the thiol group to the double bond between the carbon atoms of the maleimide compound. In this reaction, the maleimide compound represented by the following formula (2) may be replaced with a meleic hydrazide represented by the following formula (2'):

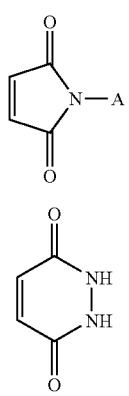

wherein A is as defined above for the formula (1').

In the method as described above, if the reactivity of the active hydrogen-containing group represented by Z is higher than that of the thiol group, the reaction may be promoted, for example, after protecting the active hydrogen-containing group with an adequate protective group.

Examples of the compound having thiol group and the active hydrogen-containing group represented by Z which may be used in the method as described above include thiosalicylic acid, 2-aminoethanethiol, 2-pyridinethiol, 4-pyridinethiol, 2-aminobenzenethiol, 4-aminobenzenethiol, 4-hydroxybenezenethiol, 2-mercaptoimidazole, 2-mercaptoimidazoline, 2-mercaptobenzimidazol, 2-mercapto-5-methylbenzimidazol, 2-mercapto-5-methoxybenzimidazol, 5-amino-1,3,4-thiadiazole-2-thiol, 3-amino-5-mercapto-1,2,4-triazole, 5-methyl-1H-1,2,4-triazole-3-thiol, methanedithiol, 1,3-butanedithiol, 1,4-butane dithiol, 2,3-butanedithiol, 1,2-benzenedithiol, 1,3-benzenedithiol, 1,4-benzenedithiol, 1,10-decanedithiol, 1,2-ethanedithiol, 1,6-hexanedithiol, 1,9-nonanedithiol, 1,8-octanedithiol, 1,5-pentanedithiol, 1,2-propanedithiol, 1,3-propanedithiol, toluene-3,4-dithiol, 3,6-dichloro-1,2-benzenedithiol, 1,5-naphthalenedithiol, 1,2-benzenedimethanethiol, 1,3-benzenedimethanethiol, 1,4-benzenedimethanethiol, 4,4'-thiobisbenzenethiol, 2,5-dimercapto-1,3,4-thiadiazole, 1,8-dimercapto-3,6-dioxaoctane, 1,5-dimercapto-3-thiapentane, 1,3,5-triazine-2,4,6-trithiol (trimercapto-triazine), 2-di-n-butylamino-4,6-dimercapto-s-triazine, 2-phenylamino-4,6-dimercapto-s-triazine, trimethylol propane tris(β-thiopropionate), trimethylol propane tris(thioglycolate), and a polythiol (such as a rubber and/or a resin modified with Thiokol or thiol).

Among these, use of an aromatic thiol or a heterocyclic thiol is preferred in view of their likeliness to undergo thermal dissociation. More specifically, use of thiosalicylic acid, 2,5-dimercapto-1,3,4-thiadiazole, 2-di-n-butylamino-4,6-dimercapto-s-triazine, 2-phenylamino-4,6-dimercapto-s-triazine, trimercapto-triazine, and 3-mercapto-1,2,4-triazole is preferred. Most preferably, thiosalicylic acid, 2,5-dimercapto-1,3,4-thiadiazole, 2-di-n-butylamino-4,6-dimercapto-s-triazine, or 2-phenylamino-4,6-dimercapto-s-triazine are used in view of their handling convenience because they are solid with no odor, and also in view of their likeliness to undergo thermal dissociation.

Exemplary maleimide compounds represented by the formula (2) used in the method as described above include compounds which have been known as N-substituted maleimides, and preferable examples are a maleimide substituted with an N-alkyl group such as N-methylmaleimide, N-ethylmaleimide, N-propylmaleimide, N-butylmaleimide, N-hexylmaleimide, or N-dichlorohexylmaleimide; a maleimide substituted with an N-cycloalkyl group such as N-cyclohexyl maleimide; and a maleimide substituted with an N-aromatic group such as N-phenylmaleimide. Among these, the preferred are N-cyclohexyl maleimide and N-phenylmaleimide in view of their availability at low price.

The method as described above may be carried out, for example, by adding the maleimide compound represented by the formula (2) to the compound having thiol group and the active hydrogen-containing group represented by Z such that the amount of the maleimide compound is 0.90 to 1.10, and preferably 0.95 to 1.05 times larger that of the compound having thiol group and the active hydrogen-containing group in molar ratio, and stirring the mixture in an organic solvent at room temperature to 150° C. for 1 to 24 hours.

The organic solvent used is not particularly limited as long as it can dissolve the compound having thiol group and the active hydrogen-containing group represented by Z and the maleimide compound represented by the formula (2). Exemplary organic solvents include acetone, methyl ethyl ketone, N-methyl-2-pyrrolidone, tetrahydrofuran, and N,N-dimethyl formamide, and among these, the preferred are methyl ethyl ketone and N,N-dimethyl formamide in view of their high solvency.

After the completion of the reaction, the reaction product may be concentrated under reduced pressure to remove the organic solvent, and the compound of the present invention is thereby obtained.

Preferred examples of the compound of the present invention include those obtainable by combining the exemplary compounds described for the compound having thiol group and the active hydrogen-containing group represented by Z and the maleimide compound represented by the formula (2). Exemplary such compounds include the compound represented by the following formula (3) obtainable from 2-di-n-butylamino-4,6-dimercapto-s-triazine and N-phenylmaleimide; the compound represented by the following formula (4) obtainable from thiosalicylic acid and N-phenylmaleimide;

and the compound represented by the following formula (5) obtainable from 2-phenylamino-4,6-dimercapto-s-triazine and N-phenylmaleimide.

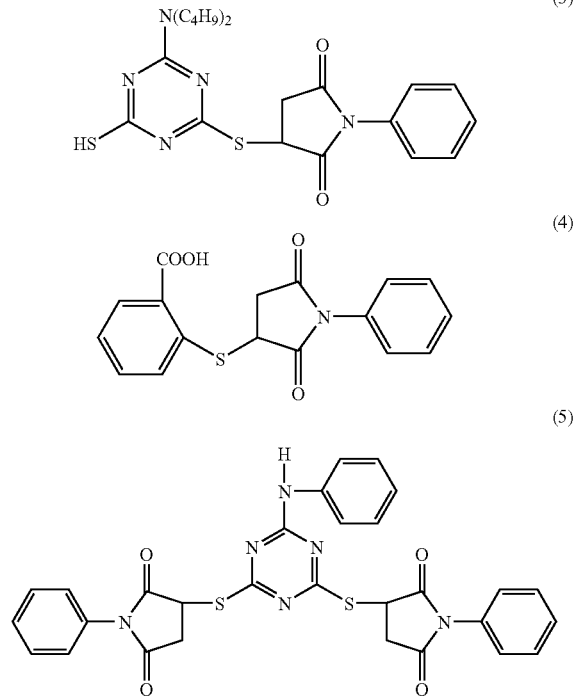

Next, the composition of the present invention is described.

The composition of the present invention contains the compound of the present invention as described above, and a rubber and/or a resin having a functional group capable of reacting with the thiol group and also having a functional group capable of reacting with the active hydrogen-containing group represented by Z.

The functional group capable of reacting with the thiol group in the rubber and/or the resin contained in the composition of the present invention is not particularly limited. This group, however, is preferably at least one member selected from the group consisting of epoxy group, isocyanate group, oxetane group, halogen group, episulfide group, silyl group, acid anhydride group (for example, cyclic acid anhydride group such as maleic anhydride group), unsaturated group (for example vinyl group), and maleimide group. The rubber and/or the resin may have one of such groups, or two or more of such groups.

The functional group capable of reacting with the active hydrogen-containing group in the rubber and/or the resin contained in the composition of the present invention is not particularly limited. This group, however, is preferably one of the groups as mentioned above for the functional group capable of reacting with the thiol group. More specifically, the functional group capable of reacting with the active hydrogen-containing group is preferably a halogen group or epoxy group when the active hydrogen-containing group is carboxy group; an acid anhydride group when the active hydrogen-containing group is hydroxy group; a halogen group or an acid anhydride group when the active hydrogen-containing group is imino group or amino group; and a halogen group, an acid anhydride group, epoxy group, or an unsaturated group when the active hydrogen-containing group is thiol group. The rubber and/or the resin may have one of such groups, or two or more of such groups.

The functional group capable of reacting with the thiol group and the functional group capable of reacting with the active hydrogen-containing group may be either the same or different.

The rubber and/or the resin contained in the composition of the present invention is not particularly limited as long as it contains the functional group capable of reacting with the thiol group and the functional group capable of reacting with the active hydrogen-containing group represented by Z.

The rubber is preferably a diene rubber, a halogenated rubber, an epoxized rubber, a maleic anhydride grafted rubber, or a vinylmethyl silicone rubber. More specifically, exemplary diene rubbers include natural rubber, butadiene rubber, isoprene rubber, chloroprene rubber, styrene-butadiene copolymer rubber, ethylene-propylene-diene copolymer rubber, and acrylonitrile-butadiene copolymer rubber, and exemplary halogenated rubbers include brominated butyl rubber, chlorinated butyl rubber and other halogenated butyl rubber, halogenated (for example, brominated) product of isobutylene-paramethylstyrene copolymer, chloroprene rubber, epichlorohydrin rubber, chlorosulfonated polyethylene, chlorinated polyethylene, maleic anhydride modified chlorinated polyethylene, chlorinated acrylic rubber, fluororubber, and acrylic rubber copolymerized with halogen monomer. Exemplary epoxized rubbers include epoxized natural rubber and epoxized acrylic rubber, and exemplary maleic anhydride grafted rubbers include maleic anhydride grafted ethylene-propylene copolymer rubber (maleic anhydride grafted EPM), maleic anhydride grafted ethylene-propylene-diene copolymer rubber, and maleic anhydride grafted butyl rubber.

Exemplary resins include epoxy resin, urethane resin, maleimide resin, and oxetane resin.

The functional group capable of reacting with the thiol group and the functional group capable of reacting with the active hydrogen-containing group is either directly bonded to the principal chain of the rubber and/or the resin or indirectly bonded to the rubber and/or the resin via its binding group (side chain).

The functional group capable of reacting with the thiol group and the functional group capable of reacting with the active hydrogen-containing group in the rubber and/or the resin contained in the composition of the present invention are not limited for their content. The content, however, is preferably such that total of both functional groups is in the range of 0.5 to 100 mol %, and more preferably in the range of 0.5 to 50 mol % in relation to the rubber and/or the resin.

The composition of the present invention comprises at least one compound of the present invention and at least one rubber and/or resin as described above.

The content of the compound of the present invention in the composition of the present invention is preferably in the range of 0.5 to 150 parts by weight, and 1 to 100 parts by weight per 100 parts by weight of the rubber and/or the resin. When the content is within such range, a sufficient amount of thiol will be generated by thermal dissociation, and crosslinking with the rubber and/or the resin will be facilitated, and as a consequence, the composition of the present invention will enjoy favorable physical properties after its curing.

The composition of the present invention according to one preferred embodiment contains magnesium oxide. Magnesium oxide scavenges the acid generated during the reaction between the active hydrogen-containing group of the compound of the present invention and the group capable of reacting with the active hydrogen-containing group of the rubber and/or the resin as described below, thereby preventing the scorching.

Magnesium oxide is preferably used at a content of 1 to 50 parts by weight, and more preferably at 1 to 10 parts by weight based on 100 parts by weight of the compound of the present invention.

In addition to the compound of the present invention, the composition of the present invention may further comprise a crosslinking agent (vulcanization agent) which is not the compound of the present invention as long as the object of the present invention is not adversely affected. Exemplary such crosslinking agent which is not the compound of the present invention include sulfur crosslinking agent, organic peroxide crosslinking agent, and phenol resin crosslinking agent. Such crosslinking agent may be used either alone or in combination of two or more.

The composition of the present invention may also contain additives such as plasticizer, filler, catalyst, solvent, UV absorber, dye, pigment, flame retardant, reinforcement, anti-aging agent, antioxidant, thixotropic agent, surfactant (including leveling agent), dispersant, dehydrating agent, rust preventive agent, tackifier, and antistatic agent. The additives used may be those commonly used for a rubber composition or a resin composition, and the additives may be used either alone or in combination of two or more.

The method used to produce the composition of the present invention is not particularly limited, and the production may be accomplished, for example, by placing the essential components and optional components as described above in a reaction container, and thoroughly stirring the mixture in a blender or the like under reduced pressure.

Mechanism of the crosslinking that takes place in the composition of the present invention and the reason for the superior storage stability and thermal stability of the composition of the present invention are deduced as described below. The scheme used in the following explanation is the reaction that is expected to have taken place in Example 1 below.

When the composition of the present invention is heated, reaction between the active hydrogen-containing group of the compound of the present invention and the functional group capable of reacting with the active hydrogen-containing group of the rubber and/or resin first occurs, and the compound of the present invention becomes bonded to the principal chain of the rubber and/or the resin (Reaction 1 in the following reaction scheme). This reaction may partly take place during the storage of the present composition before its heating. The acid generated in this reaction is captured by magnesium oxide.

When the heating is continued, the compound of the present invention that had been bonded to the principal chain of the rubber and/or the resin undergoes thermal dissociation by the heat, and maleimide compound becomes detached to generate thiol group (Reaction 2 in the following reaction scheme).

The thiol group generated then reacts with and become bonded to the functional group capable of reacting with the thiol group of the rubber and/or the resin. In other words, the principal chain of the rubber and/or the resin becomes crosslinked to each other by the compound of the present invention.

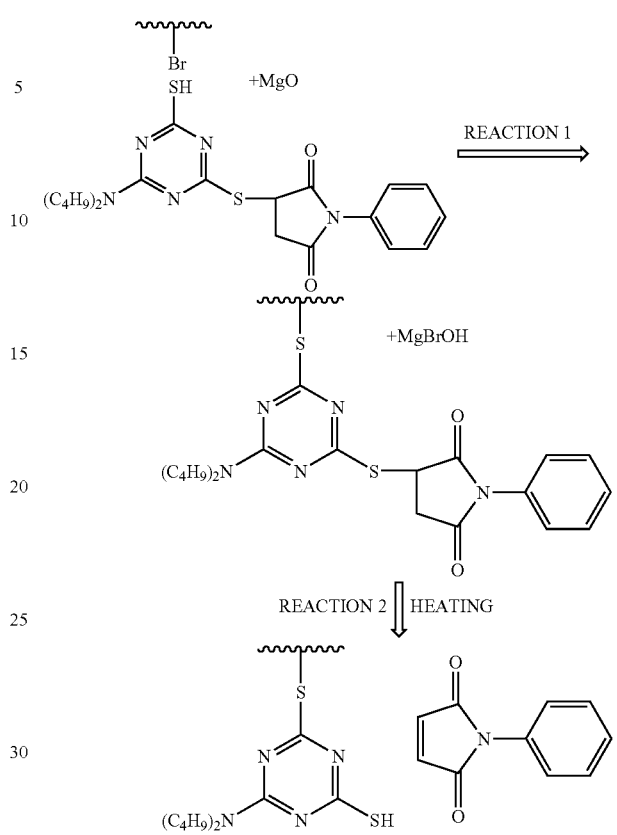

In the case of the compound of the present invention containing only one active hydrogen-containing group per molecule, crosslinking does not take place even if the active hydrogen-containing group reacts with the rubber and/or the resin during the room temperature storage or in the heating stage before reaching the vulcanization temperature, and the product is free from the problems of storage stability or scorching. When the composition contains magnesium oxide, the acid generated in the step as described above is captured, and scorching is thereby prevented.

In the meanwhile, the compound of the present invention has its thiol group protected by the maleimide compound in its molecule, and this maleimide compound becomes detached at the predetermined temperature range (for example, at 160 to 180° C.). If the vulcanization temperature is designed to be within such temperature range, crosslinking starts as soon as the temperature reaches the vulcanization temperature in the course of vulcanization. The detached maleimide compound, then, functions as a radical scavenger, and even if a high vulcanization temperature (for example, 200° C.) were used, decomposition of the principal chain of the rubber and/or the resin is suppressed, and the thermal stability is thereby improved.

When the composition of the present invention contains both the halogenated rubber and the diene rubber, co-vulcanization of the halogenated rubber and the diene rubber can be realized by further incorporating sulfur in the composition, for example, as described below.

First, the composition of the present invention containing the compound of the present invention and the halogenated rubber is heated. The active hydrogen-containing group of the compound of the present invention, then, reacts with the carbon-bromine bond of the halogenated rubber, and the compound of the present invention binds to the principal chain of the rubber (Reaction 3 in the following reaction scheme). The diene rubber and the sulfur are then added to the composition of the present invention after the Reaction 3. When the heating is continued, the diene rubber is vulcanized by the sulfur, and simultaneously, the compound of the present invention that had bonded to the principal chain of the rubber becomes dissociated by the heat. The maleimide compound is thereby detached to generate thiol group, and the thus generated thiol group and the double bond of the diene rubber react to become bonded (Reaction 4 in the following reaction scheme). The co-vulcanization of the halogenated rubber and the diene rubber are thereby accomplished.

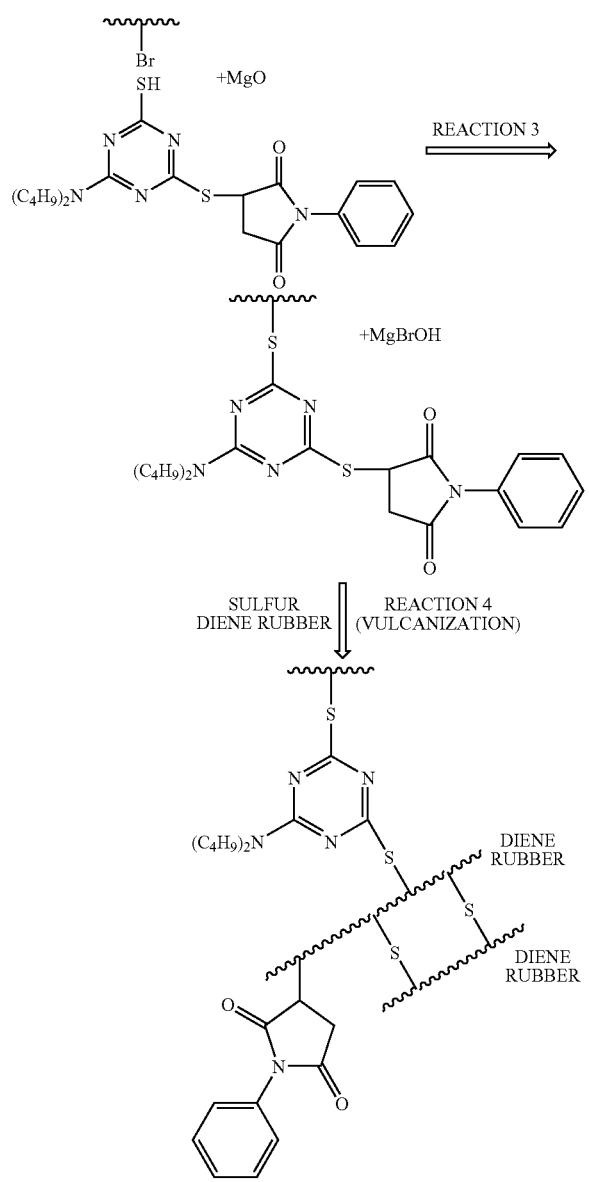

When the composition of the present invention comprises 100 parts by weight of the rubber including the rubber (A) having halogen group and/or an acid anhydride group and in which content of the unsaturated bond is up to 30 wt %; 0.1 to 20 parts by weight of the compound of the present invention; and at least one crosslinking agent selected from the group consisting of sulfur, organic peroxide, quinone dioxime, metal oxide, and alkylphenol formaldehyde resin, the composition of the present invention may be laminated with a rubber composition vulcanizable with sulfur and the layers may be adhered to each other by vulcanization to thereby produce a rubber laminate. In this case, reactions like those of Reactions 3 and 4 as described above take place at the interface between the rubber composition of the present invention and the sulfur-vulcanizable rubber composition, and these compositions adhere to one another by co-vulcanization. As described above, a halogenated butyl rubber can be adhered to a sulfur vulcanizable rubber such as diene rubber by vulcanization, realizing the type of lamination that could not have been accomplished by the prior art techniques.

The rubber (A) preferably contains at least one member selected from the group consisting of halogenated butyl rubber, butyl rubber modified with maleic anhydride, ethylene-propylene copolymer rubber modified with maleic anhydride, ethylene-propylene-diene copolymer rubber modified with maleic anhydride, halogenated isobutylene-paramethylstyrene copolymer, chlorosulfonated polyethylene, epichlorohydrin rubber, fluororubber, and an acryl rubber having a halogen monomer copolymerized therein.

The composition of the present invention may contain a rubber other than the rubber (A). Exemplary such rubbers which may be used include the rubbers known in the art.

Content of the unsaturated bond in the rubber (A) is up to 30 wt %. In the case of conventional rubbers, the rubber could not be adhered to a rubber vulcanizable with sulfur such as diene rubber when the content of the unsaturated bond was in such range. Use of the compound of the present invention has enabled such adhesion.

Examples of the rubber vulcanizable with sulfur include diene rubber, ethylene-propylene-diene copolymer rubber (EPDM), norbornene rubber (NOR), and epichlorohydrin-allyl glycidyl ether copolymer rubber (GCO, GECO).

Exemplary organic peroxides include dicumyl peroxide, di-t-butylperoxide, t-butylcumyl peroxide, benzoylperoxide, 2,5-dimethyl-2,5-di(t-butylperoxy)hexyne-3,2,5-dimethyl-2,5-di(t-butylperoxy)hexane, 1,3-bis(t-butylperoxy isopropyl) benzene, and n-butyl 4,4-di-t-butylperoxy-valerate.

Exemplary metal oxides include zinc oxide and magnesium oxide.

The compound of the present invention is preferably used at 0.1 to 20 parts by weight in relation to 100 parts by weight of the rubber including the rubber (A). When the compound of the present invention is used in such range, the product will exhibit practically acceptable strength and rubber elasticity.

In this case, the composition may preferably further comprise a sulfenamide or a thiuram vulcanization accelerator, and inclusion of such vulcanization accelerator results in the accelerated vulcanization, and hence, improved physical properties.

Exemplary sulfenamide vulcanization accelerators include N-cyclohexyl-2-benzothiazolyl sulfenamide, N-t-butyl-2-benzothiazolyl sulfenamide, N-oxydiethylene-2-benzothiazolyl sulfenamide, and N,N'-dicyclohexyl-2-benzothiazolyl sulfenamide.

Exemplary thiuram vulcanization accelerators include tetrakis(2-ethylhexyl)thiuram disulfide, tetramethylthiuram disulfide, tetraethylthiuram disulfide, tetramethylthiuram monosulfide, and dipentamethylenethiuram tetrasulfide.

The composition of the present invention may be used in various products such as adhesives, tackifiers, coating composition, and sealants.

EXAMPLES

Next, the present invention is described by referring to the Examples which by no means limit the scope of the present invention.

1-1. Synthesis of the Compounds

Synthesis Example 1

27.2 g (0.1 mol) of 2-di-n-butylamino-4,6-dimercapto-s-triazine and 17.3 g (0.1 mol) of N-phenylmaleimide were reacted in 150 g of methyl ethyl ketone at 90° C. for 5 hours. After the completion of the reaction, the reaction product was concentrated at 90° C. under reduced pressure to produce 44.3 g of Compound 1 represented by formula (3) as described above (yield, 99%).

Synthesis Example 2

15.4 g (0.1 mol) of thiosalicylic acid and 17.3 g (0.1 mol) of N-phenylmaleimide were reacted in 150 g of methyl ethyl ketone at 90° C. for 5 hours. After the completion of the reaction, the reaction product was concentrated at 90° C. under reduced pressure to produce 32.5 g of Compound 2 represented by the formula (4) as described above (yield, 99%).

1-2. Preparation of the Rubber Composition

The components shown in Table 1 below were blended by the composition (parts by weight) shown in Table 1 to thereby produce the rubber compositions.

TABLE 1

| | Comparative Example 1 | Comparative Example 2 | Example 1 | Example 2 |
|---|---|---|---|---|
| Br-IIR | 100 | 100 | 100 | 100 |
| GRF grade carbon black | 60 | 60 | 60 | 60 |
| Stearic acid | 1 | 1 | 1 | 1 |
| Petroleum pitch | 5 | 5 | 5 | 5 |
| Petroleum resin | 5 | 5 | 5 | 5 |
| Paraffin oil | 10 | 10 | 10 | 10 |
| ZnO | 5 | | | |
| MgO | | 5 | 5 | 5 |
| Compound 1 | | | 4.6 | |
| Compound 2 | | | | 3.3 |

The components shown in Table 1 are as described below.
Br-IIR (brominated butyl rubber): manufactured by Bayer Polysar B.N.Y
GPF grade carbon black: manufactured by Mitsubishi Chemical
Stearic acid: manufactured by Nippon Yushi (NOF)
Petroleum pitch: manufactured by Sumikin Chemical Industry
Petroleum resin: manufactured by Exxon chem.
Paraffin oil: manufactured by Showa Shell Sekiyu
ZnO: manufactured by Shodo Chemical
MgO: manufactured by Kyowa Chemical Industry
Compound 1: Compound 1 obtained in the Synthesis Example 1
Compound 2: Compound 2 obtained in the Synthesis Example 2

1-3. Evaluation of the Rubber Composition

The thus produced rubber compositions were vulcanized at the temperature shown in Table 2 for 20 minutes, and vulcanized sheets of 15 cm×15 cm×2 mm were produced. From this vulcanized sheet, dumbbell shaped test pieces according to JIS No. 3 were blanked. The test piece was pulled at a speed of 500 mm/min to measure tensile stress at break ($T_B$) and elongation at brake ($E_B$)

The results are shown in Table 2.

TABLE 2

| Curing temp. (° C.) | Physical property values | Comp. Ex. 1 | Comp. Ex. 2 | Ex. 1 | Ex. 2 |
|---|---|---|---|---|---|
| 140 | $T_B$ (MPa) | 1.50 | 0.45 | 4.80 | 0.65 |
| | $E_B$ (%) | 1000 | 1500 | 370 | 1500 |
| 160 | $T_B$ (MPa) | 8.06 | 0.71 | 6.52 | 2.01 |
| | $E_B$ (%) | 675 | 1385 | 325 | 885 |
| 180 | $T_B$ (MPa) | 7.31 | 1.56 | 6.36 | 7.30 |
| | $E_B$ (%) | 655 | 1155 | 280 | 655 |
| 200 | $T_B$ (MPa) | 7.05 | 2.41 | 8.73 | 9.17 |
| | $E_B$ (%) | 710 | 975 | 265 | 645 |

As demonstrated in Table 2, the composition of the present invention (Example 1) produced by using the Compound 1 which is the compounds of the present invention exhibited a $T_B$ which is equivalent to that of the conventional brominated butyl rubber composition (Comparative Example 1) prepared by using zinc oxide for the curing agent at a vulcanization temperature of 160 to 200° C. In the meanwhile, the composition prepared by using magnesium oxide instead of the zinc oxide (Comparative Example 2) exhibited a lower $T_B$ and a higher $E_B$, indicating that this composition did not become crosslinked at such temperature. These results suggest that, in the case of the composition of the present invention (Example 1), the compound of the present invention which bonded to the brominated butyl rubber in the stage of heating up to the vulcanization temperature became dissociated by the heat applied during the vulcanization to cause detachment of the maleimide compound thereby forming thiol group, and this thiol group further reacted with the brominated butyl rubber to cause the crosskinking.

The situation seems to be similar for the composition of the present invention (Example 2) produced by using the Compound 2 which is also the compounds of the present invention. In this case, however, the composition did not become crosslinked at the vulcanization temperature of 140° C. as clearly indicated by the low $T_B$. In other words, Example 2 is different at this point from Example 1 which became crosslinked at the vulcanization temperature 140° C.

Accordingly, it can be deduced from the comparison of the Example 1 and Example 2 that the vulcanization temperature (the temperature of the crosslinking) of the composition of the present invention can be regulated by adequately selecting "X" in the compound of the present invention.

It is to be noted that the compositions of the present invention (Examples 1 and 2) produced by using the compounds of the present invention did not exhibit rubber scorching during the storage at room temperature and in the heating stage before reaching the vulcanization temperature in the course of the vulcanization.

2-1. Synthesis of the Compound

Synthesis Example 3

23.6 g (0.1 mol) of 2-phenylamino-4,6-dimercapto-s-triazine and 34.6 g (0.2 mol) of N-phenylmaleimide were reacted in 150 g of dimethyl formamide at 90° C. for 5 hours. After completion of the reaction, the reaction product was concentrated at 100° C. under reduced pressure to produce 56.3 g of Compound 3 represented by the formula (5) as described above (yield, 97%).

2-2. Preparation of the Rubber Composition

The components shown in Table 3 below were blended by the composition (parts by weight) shown in Table 3 to produce the rubber compositions.

TABLE 3

|  | Comparative Example 3 | Example 3 |
| --- | --- | --- |
| Br-IIR | 100 | 100 |
| FEF grade carbon black | 60 | 60 |
| Stearic acid | 1 | 1 |
| Aroma oil | 10 | 10 |
| Aromatic petroleum resin | 5 | 5 |
| ZnO | 3 |  |
| MgO |  | 3 |
| Sulfur | 0.3 |  |
| Vulcanization accelerator | 1 |  |
| Compound 3 |  | 6 |

The components shown in Table 3 are as described below.
Br-IIR (brominated butyl rubber): Bayer Bromobutyl X2 manufactured by Bayer
FEF grade carbon black: HTC#100 manufactured by Shin-Nippon Carbon
Stearic acid: stearic acid beads manufactured by Nippon Yushi (NOF)
Aroma oil: Extract No. 4S manufactured by Showa Shell Sekiyu
Aromatic petroleum resin: FR-120 manufactured by Sumikin Air Water Chemical
ZnO: zinc white #3 manufactured by Shodo Chemical
MgO: manufactured by Kyowa Chemical Industry
Sulfur: sulfur fine powder manufactured by Tsurumi Chemical Industry
Vulcanization accelerator: dibenzothiazyl disulfide, Nocceler DM manufactured by Ouchishinko Chemical Industrial
Compound 3: Compound 3 obtained in the Synthesis Example 3

2-3. Evaluation of the Rubber Composition

The thus produced rubber compositions were evaluated for their physical properties as described below.

(1) Mooney Scorch Time

Unvulcanized rubber composition was continuously measured for its Mooney viscosity by using L-shaped rotor according to the procedure defined in JIS K6300-1994 under the conditions including preheating time of 1 minute and test temperature of 125° C. The minimum value of the Mooney viscosity was designated $V_m$. Mooney scorch time was also determined by measuring the time that took the Mooney viscosity to increase 5 points from the $V_m$.

The results are shown in Table 4. Mooney scorch time is an index for scorching (the scorching of rubber), and a longer scorch time is preferable.

(2) Initial Physical Properties of the Material, High Temperature Physical Properties of the Material, and Retention of the Physical Properties The thus produced rubber compositions were vulcanized at 180° C. for 10 minutes, and vulcanized sheets of 15 cm×15 cm×2 mm were produced. From this vulcanized sheet, dumbbell shaped test pieces according to JIS No. 3 were blanked.

Next, the test piece was pulled at room temperature at a speed of 500 mm/min to measure modulus at 100% elongation ($M_{100}$), tensile stress at break ($T_B$), and elongation at break ($E_B$), thereby obtaining initial physical properties of the material. The test piece was also measured in the same way in an atmosphere at 100° C. to thereby determine high temperature physical properties of the material. Next, the values of the high temperature physical properties were respectively divided by the values of the initial physical properties to calculate retention of the physical properties.

The results are shown in Table 4.

TABLE 4

|  | Comparative Example 3 | Example 3 |
| --- | --- | --- |
| Mooney scorch time (min) | 15.9 | >45 |
| Initial physical properties |  |  |
| $M_{100}$ (MPa) | 1.0 | 1.2 |
| $T_B$ (MPa) | 9.0 | 9.0 |
| $E_B$ (%) | 880 | 770 |
| High temperature physical properties |  |  |
| $M_{100}$ (MPa) | 0.5 | 0.8 |
| $T_B$ (MPa) | 4.2 | 4.8 |
| $E_B$ (%) | 800 | 753 |
| Retention of the physical properties |  |  |
| $M_{100}$ (%) | 50 | 67 |
| $T_B$ (%) | 47 | 53 |
| $E_B$ (%) | 90.9 | 97.8 |

As demonstrated in Table 4, the composition of the present invention (Example 3) produced by using the Compound 3 which is the compounds of the present invention exhibited longer Mooney scorch time and superior retention of the physical properties at high temperature compared to the use of zinc oxide (Comparative Example 3).

3-1. Preparation of the Rubber Composition

The components shown in Table 5 below were blended by the composition (parts by weight) shown in Table 5 to produce the rubber compositions.

TABLE 5

|  | Comp. Ex. 4 | Comp. Ex. 5 | Ex. 4 | Ex. 5 | Ex. 6 | Ex. 7 | Ex. 8 | Ex. 9 | Ex. 10 |
| --- | --- | --- | --- | --- | --- | --- | --- | --- | --- |
| Natural rubber | 40 |  | 40 |  |  |  |  |  |  |
| Br-IIR | 60 | 100 | 60 | 100 | 100 | 100 | 100 | 100 |  |
| Maleic anhydride grafted EPM |  |  |  |  |  |  |  |  | 100 |
| FEF grade carbon black | 50 | 60 | 50 | 60 | 60 | 60 | 60 | 60 | 60 |

TABLE 5-continued

| | Comp. Ex. 4 | Comp. Ex. 5 | Ex. 4 | Ex. 5 | Ex. 6 | Ex. 7 | Ex. 8 | Ex. 9 | Ex. 10 |
|---|---|---|---|---|---|---|---|---|---|
| Stearic acid | 1 | 1 | 1 | 1 | 1 | 1 | 1 | 1 | 1 |
| Aroma oil | 10 | 10 | 10 | 10 | 10 | 10 | 10 | 10 | 10 |
| Aromatic petroleum resin | 5 | 5 | 5 | 5 | 5 | 5 | 5 | 5 | 5 |
| ZnO | 3 | 3 | 3 | 3 | 3 | 3 | 3 | 3 | 3 |
| Sulfur | 1 | 0.3 | | | 0.3 | 0.3 | 0.3 | | 0.3 |
| Organic peroxide | | | | | | | | 0.7 | |
| Vulcanization accelerator 1 | 1 | 1 | | | 1 | | | | 1 |
| Vulcanization accelerator 2 | | | | | | 1 | | | |
| Vulcanization accelerator 3 | | | | | | | 2 | | |
| Compound 2 | | | 4 | 4 | 4 | 4 | 4 | 4 | |
| Compound 3 | | | | | | | | | 4 |
| $M_{100}$ (MPa) | 1.2 | 1.0 | 1.0 | 1.2 | 1.2 | 1.3 | 1.1 | 1.2 | 1.0 |
| $T_B$ (MPa) | 9.5 | 9.0 | 9.6 | 7.6 | 8.2 | 9.0 | 8.5 | 8.3 | 6.9 |
| $E_B$ (%) | 610 | 800 | 700 | 670 | 810 | 850 | 900 | 810 | 680 |
| Peel strength (N/25 mm) | 440 | 300 | 750 | 520 | 680 | 550 | 750 | 460 | 590 |
| State of the peeling | Peeling at interface | Peeling at interface | Material fracture | Material fracture | Material fracture | Material fracture | Material fracture | Material fracture | Material fracture |

The components shown in Table 5 are as described below.

Natural rubber: TSR20

Br-IIR (brominated butyl rubber): Bayer Bromobutyl X2 manufactured by Bayer; content of unsaturated bond, up to 5.0 wt %

Maleic anhydride grafted EPM: Tafiner manufactured by Mitsui Chemical

FEF grade carbon black: HTC#100 manufactured by Shin-Nippon Carbon

Stearic acid: stearic acid beads manufactured by Nippon Yushi (NOF)

Aroma oil: Extract No. 4S manufactured by Showa Shell Sekiyu

Aromatic petroleum resin: FR-120 manufactured by Sumikin Air Water Chemical

ZnO: zinc white #3 manufactured by Shodo Chemical

Sulfur: sulfur fine powder manufactured by Tsurumi Chemical Industry

Organic peroxide: dicumyl peroxide, PERCUMYL D-40 manufactured by Nippon Yushi (NOF), purity 40 wt %

Vulcanization accelerator 1: dibenzothiazyl disulfide, Nocceler DM manufactured by Ouchishinko Chemical Industrial Vulcanization accelerator 2: N-t-butyl-2-benzothiazolyl sulfenamide, Nocceler NS-F manufactured by Ouchishinko Chemical Industrial Vulcanization accelerator 3: tetrakis(2-ethylhexyl) thiuram disulfide, Nocceler TOT-N manufactured by Ouchishinko Chemical Industrial Compound 2: Compound 2 obtained in the Synthesis Example 2

Compound 3: Compound 3 obtained in the Synthesis Example 3

3-2. Evaluation of the Rubber Composition

The thus produced rubber compositions were evaluated for their physical properties as described below.

(1) Physical Properties of the Material

The thus produced rubber compositions were vulcanized at 180° C. for 15 minutes, and vulcanized sheets of 15 cm×15 cm×2 mm were produced. From this vulcanized sheet, dumbbell shaped test pieces according to JIS No. 3 were blanked.

Next, the test piece was pulled at room temperature at a speed of 500 mm/min to measure modulus at 100% elongation ($M_{100}$), tensile stress at break ($T_B$), and elongation at break ($E_B$)

The results are shown in Table 5.

(2) Adhesion with a Diene Rubber

The thus produced rubber composition was laminated with the rubber composition for peel test produced by blending the components shown in Table 6 according to the composition (parts by weight) shown in Table 6, and after disposing a liner fabric on both sides of the laminate, the laminate was vulcanized at 180° C. for 15 minutes.

Peel test was then conducted by using a rectangular test piece cut out of the laminate to a width of 25 mm on an autograph. In the peel test, peel strength was measured, and the state of peeling was visually observed. The state of peeling was visually evaluated by observing the peel surface of the test piece after the peel test to determine whether the peeling occurred at the boundary or the material fracture had occurred at either of the rubber composition.

The results are shown in Table 5.

TABLE 6

| | |
|---|---|
| Natural rubber | 60 |
| Styrene-butadiene rubber | 40 |
| FEF grade carbon black | 50 |
| ZnO | 5 |
| Stearic acid | 1 |
| Aroma oil | 10 |
| Sulfur | 2.5 |
| Vulcanization accelerator | 1.5 |

The components shown in Table 6 are as described below.

Natural rubber: TSR20

Styrene-butadiene rubber: Nipol 1502 manufactured by Nippon Zeon

FEF grade carbon black: HTC#100 manufactured by Shin-Nippon Carbon

ZnO: zinc white #3 manufactured by Shodo Chemical

Stearic acid: stearic acid beads manufactured by Nippon Yushi (NOF)

Aroma oil: Extract No. 4S manufactured by Showa Shell Sekiyu

Sulfur: Crystex HSOT 20 manufactured by Flexsys

Vulcanization accelerator: Nocceler NS-F manufactured by Ouchishinko Chemical Industrial As demonstrated in Table 5, the rubber laminates of the present invention (Examples 4 to 10) produced by using the Compound 2 or 3 which are the compounds of the present invention exhibited good adhesion between the halogenated rubber or the maleic anhydride grafted rubber and the diene rubber.

In contrast, the laminate produced without using the compound of the present invention (Comparative Examples 4 and 5) exhibited poor adhesion between the halogenated rubber and the diene rubber.

The invention claimed is:

1. A composition comprising:
a compound represented by the following formula (1')

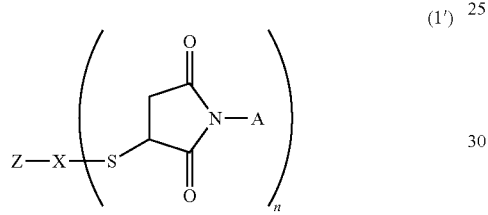

in the formula, Z represents thiol group or carboxy group; X represents an aromatic group containing 6 to 18 atoms (the number not including hydrogen), or a traizine group, which may be optionally substituted and which may contain at least one member selected from $SO_2$, O, N, and S; A which is included at a number of n independently represents an optionally substituted organic group containing 1 to 24 carbon atoms which does not contain active hydrogen group; and n represents an integer of 1 to 4, and and a rubber comprising at least one member selected from the group consisting of diene rubber, halogenated rubber, maleic anhydride grafted rubber and epoxidized rubber which has a functional group capable of reacting with thiol group and a functional group capable of reacting with the active hydrogen-containing group represented by Z.

2. The composition according to claim 1 further comprising magnesium oxide.

3. A composition comprising:
(A) 100 parts by weight of a rubber including rubber (A) containing a halogen group and/or an acid anhydride group, and containing 30 wt % or less of unsaturated bond,
(B) 1 to 20 parts by weight of a compound represented by the following formula (1')

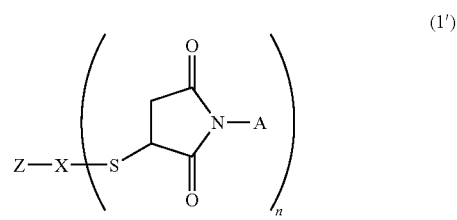

in the formula, Z represents thiol group or carboxy group; X represents an aromatic group containing 6 to 18 atoms (the number not including hydrogen), or a traizine group, which may be optionally substituted and which may contain at least one member selected from $SO_2$, O, N and S; A which is included at a number of n independently represents an optionally substituted organic group containing 1 to 24 carbon atoms which does not contain active hydrogen group; and n represents an integer of 1 to 4 and
(C) at least one crosslinking agent selected from the group consisting of sulfur, organic peroxide, quinone dioxime, metal oxide, and alkylphenol-formaldehyde resin.

4. The composition according to claim 3 comprising at least one member selected from the group consisting of halogenated butyl rubber, maleic anhydride grafted butyl rubber, maleic anhydride grafted ethylene-propylene copolymer rubber, maleic anhydride grafted ethylene-propylene-diene copolymer rubber, halogenated isobutylene-paramethylstyrene copolymer, chlorosulfonated polyethylene, epichlorohydrin rubber, fluoro rubber, and an acryl rubber having a halogen monomer copolymerized therein as the rubber (A).

5. The composition according to claim 3 or 4 further comprising a sulfenamide or thiuram vulcanization accelerator.

6. A rubber laminate obtainable by disposing the composition according to claim 3 or 4 on a sulfur-vulcanizable rubber composition, and adhering these compositions by vulcanization.

* * * * *